United States Patent
Hansen et al.

(10) Patent No.: US 6,573,398 B2
(45) Date of Patent: Jun. 3, 2003

(54) SECONDARY ASPARTIC ACID AMIDE ESTERS

(75) Inventors: Richard G. Hansen, Mahtomedi, MN (US); Dean M. Moren, North St. Paul, MN (US); Mark D. Purgett, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/200,789

(22) Filed: Jul. 22, 2002

(65) Prior Publication Data

US 2003/0004367 A1 Jan. 2, 2003

Related U.S. Application Data

(62) Division of application No. 09/379,397, filed on Aug. 24, 1999, now Pat. No. 6,469,199, which is a division of application No. 09/109,588, filed on Jul. 2, 1998, now Pat. No. 6,005,062.

(51) Int. Cl.$^7$ .................... C07C 227/22; C07C 229/08
(52) U.S. Cl. .................... 560/19; 560/155; 549/479
(58) Field of Search .................... 560/19, 155; 549/479

(56) References Cited

U.S. PATENT DOCUMENTS

| | | | |
|---|---|---|---|
| 3,001,973 A | 9/1961 | Piepenbrink et al. |
| 3,124,605 A | 3/1964 | Wagner et al. |
| 3,152,162 A | 10/1964 | Fischer et al. |
| 3,201,372 A | 8/1965 | Wagner et al. |
| 3,228,972 A | 1/1966 | Schwartz |
| 3,394,164 A | 7/1968 | McClellan et al. |
| 3,644,457 A | 2/1972 | Konig et al. |
| 3,814,776 A | 6/1974 | Fischer et al. |
| 4,169,931 A | 10/1979 | Rottmaier et al. |
| 4,687,813 A | 8/1987 | Lenz et al. |
| 5,126,170 A | 6/1992 | Zwiener et al. |
| 5,236,741 A | 8/1993 | Zwiener et al. |
| 5,243,012 A | 9/1993 | Wicks et al. |
| 5,412,056 A | 5/1995 | Zwiener et al. |
| 5,478,596 A | 12/1995 | Gurney |
| 5,516,873 A | 5/1996 | Hicks et al. |
| 5,580,945 A | 12/1996 | Wade et al. |

FOREIGN PATENT DOCUMENTS

| | | |
|---|---|---|
| BE | 752261 | 12/1970 |
| BE | 761626 | 6/1971 |
| DE | PS-1022789 | 9/1956 |
| DE | PS-1027394 | 10/1956 |
| DE | OS-1101394 | 4/1958 |
| DE | OP-1092007 | 7/1959 |
| DE | 2004048 | 12/1970 |
| DE | 1929034 | 4/1972 |
| DE | OS 2158945 | 5/1973 |
| DE | 2504400 | 8/1976 |
| DE | 2537685 | 3/1977 |
| DE | 2552350 | 5/1977 |
| GB | PS-994890 | 12/1962 |
| NL | 7102524 | 8/1971 |
| WO | WO 97/03252 | 1/1997 |

OTHER PUBLICATIONS

Martin et al., J. Org. Chem., vol. 25, No. 11, pp 3814–3818, 1970.
Boyd et al. J.C.S., Perk I, pp 1338–1350, 1978.
Aebi et al, Helv. Chim. Acta, vol. 68, pp 1507–1518, 1985.
Transportation Research Record 1409, By Hedblom et al, Published 1994 "Correlation of the Nighttime Visibility of Pavement Marking Tapes with Photometric Measurement".
Rolf, Paul et al., "A Mechanism for the N,N'-Dicyclohexylcarbodiimide–Caused Dehydration of Asparagine and Maleamic Acid Derivatives"; *Journal of the American Chemical Society*, vol. 86, No. 19, Oct. 5, 1964, pp. 4162–4166.
G. Schroeter et al., "Ueber das alpha–Anilidobrenzweinestersaurenitril und seine Umwandlungsproducte"; *Berichte Der Deutschen Chemischen Gesellschaft*, vol. 35, 1902, pp. 2078–2080.
[English translation] Gavryushina, V.M. et al., "Structure of the Products from the Addition of Amines to Ethyl N,N–Diethylfumaramate"; *Zhurnal Organicheskoi Khimii*, vol. 23, No. 2, pp. 317–324, 1987.
Chemical Abstracts, "Structure of Amine Adducts with Ethyl N,N–diethylfumaramate", V. M. Gavryushina et al., vol. 107, No. 19, p. 669, Nov. 9, 1987.

*Primary Examiner*—Shailendra Kumar
(74) *Attorney, Agent, or Firm*—Carolyn A. Fischer

(57) ABSTRACT

New secondary amines are described which are prepared from inexpensive, commercially available raw materials, are stable at room temperature, and are reactive toward electrophiles. The secondary amines are prepared by the addition of one or more primary amines with one or more male (amide/ester) and fumar (amide/ester) Michael receptors. The above amines can be used as coreactants with aliphatic polyisocyanates for polyurea coatings. The novel secondary amines are also described as particularly useful as part of a two-part liquid pavement marking composition for pavement markings.

4 Claims, No Drawings

SECONDARY ASPARTIC ACID AMIDE ESTERS

This is a division of application Ser. No. 09/379,397 filed Aug. 24, 1999, now U.S. Pat. No. 6,469,199, which is a division of application Ser. No. 09/109,588 filed Jul. 2, 1998, now U.S. Pat. No. 6,005,062.

FIELD OF THE INVENTION

The invention relates generally to new secondary amines and their use in coatings, e.g. polyurea coatings and in a liquid pavement marking composition.

BACKGROUND OF THE INVENTION

Polyfunctional amines are used as coreactants with polyfunctional isocyanates in many applications. These reactions yield polyureas which are a highly regarded class of polymers, known for their toughness, high strength and dynamic mechanical and high temperature performance. These reactions are generally carried out in specialized equipment, due to the high reactivity of amines and isocyanates. This has limited their use in traditional adhesives, coatings and sealer type product applications.

Typical primary and secondary amines are extremely reactive with a variety of electrophiles, which results in very short gel times with little or no potlife. The reaction of primary amines with isocyanates is extremely exothermic and produces strongly hydrogen bonded dihydro-urea linkages. Strongly hydrogen bonded groups may disadvantageously increase product viscosities and hinder subsequent mobility and reactivity of attached functional groups. Additionally, uncontrollable reaction rates are undesirable in many applications.

The utility of amines of the present invention is based on the addition reaction between a polyisocyanate component and an isocyanate-reactive component, in particular polyamines containing secondary amino groups. This reaction is known in principle from DE-OS 2,158,945 (Fed. Rep. Of German, 1973) but according to the teachings of this publication the reaction is not used for crosslinking two-component coating compositions at relatively low temperatures but rather for the preparation of intermediate products which are converted at elevated temperatures into heterocyclic end products.

Bayer Corp. has recently introduced polyaspartic acid diesters under the name DESMOPHEN™. These secondary amines react more controllably with electrophiles than do the corresponding primary amines. However, the adducts of these amines and isocyanates are capable of a further transformation to form a hydantoin ring structure, giving rise to shrinking of the coating and generating undesired alcohol byproducts.

U.S. Pat. No. 5,126,170 describes secondary amines, referred to as "polyaspartic acid derivatives", which are formed by the Michael-type reaction of primary polyamines with maleic or fumaric acid ester Michael receptors. This reaction is illustrated below as formula (I), wherein $R_1$, $R_2$ and $R_3$ are as defined in the cited reference.

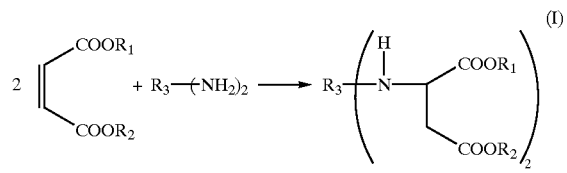

These aspartic ester diesters react with isocyanates to form urea-diester linkages. This reaction is illustrated below as formula (II), wherein $R_1$, $R_2$, $R_3$ and $R_4$ are as defined in the cited reference.

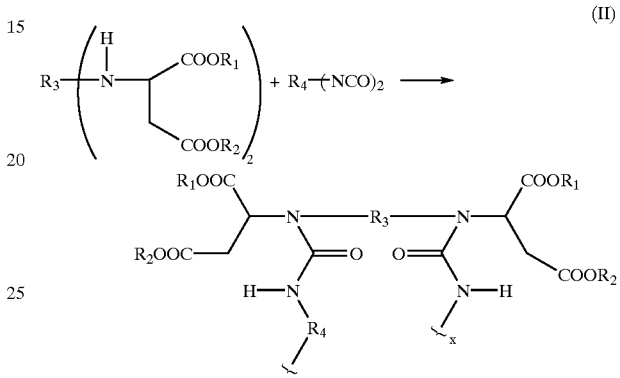

Urea-diester linkages are reportedly unstable however, cyclizing to the hydantoin with the concomitant expulsion of alcohol. The expelled alcohol is problematic in some systems such as isocyanate-terminated prepolymers, since it may undesirably react with residual isocyanate groups. Dimensional changes of the polymer upon hydantoin formation is a potential problem as well. This reaction is illustrated below as formula (III), wherein $R_1$, $R_2$, $R_3$ and $R_4$ are as defined in the cited reference.

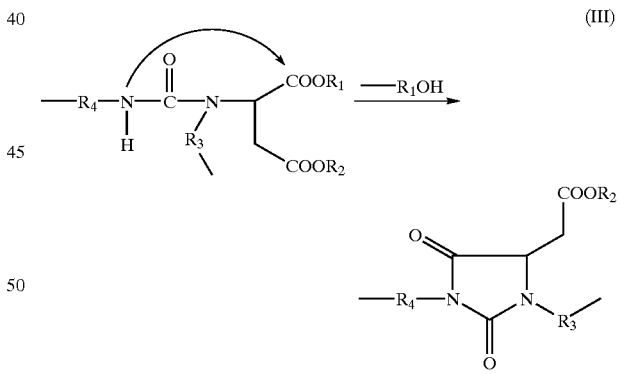

In addition to U.S. Pat. No. 5,126,170, the above aspartic ester diesters are described to be suitable for manufacture of high performance polyurethane or polyurea coatings for specific end-use applications in U.S. Pat. Nos.: 5,236,741, 5,243,012, 5,412,056, 5,516,873 and 5,580,945.

There is a need for improved polyurea and polyurethane coatings having amine components that resist hydantoin formation.

There is a significant need for a liquid pavement marking composition that will provide increased durability and retained reflectivity once applied to a surface and dried or cured. Furthermore, it is advantageous to apply markings in a wider range of weather conditions than is possible with existing compositions. There is also a need for marking compositions with improved cure profiles to ensure both substrate wet out and rapid track free time. Improvements are needed to obtain compositions that are substantially free of volatile organic components. Compositions of this type are typically used on roads, highways, parking lots and recreational trails to form stripes, bars and markings for the delineation of lanes, crosswalks, parking spaces, symbols and legends and the like. They are typically applied by spray coating (i.e., painting) the pavement surface. Preformed pavement marking sheets or tapes have also been used to mark pavement or traffic bearing surfaces.

Pavement marking stripes, or pavement markings of other shapes, may include reflective optical elements adhered to the pavement surface by the use of a binder. Current traffic paint systems typically use conventional $1.5n_D$ glass microspheres for increased retroreflection. The microspheres are typically flood coated onto the wet marking immediately after coating. This provides the paint with improved retroreflectivity and also covers the top surface of the uncured or undried coating with a protective layer of microspheres. This protective layer allows the markings to be exposed to traffic sooner because of the layer of microspheres over the surface, which prevents transfer of the coating to the surface of vehicle tires. This is important for rates of marking application. The time between application and the point where material will no longer transfer to vehicle tires is defined as the "track free" time. Shorter track free times increase marking efficiency by reducing or eliminating the need for traffic disruption through such measures as closing lanes or placing traffic control devices to protect such markings.

U.S. Pat. No. 5,478,596 discloses liquid pavement marking compositions that solve many of the problems of alkyd-based and epoxy-based pavement marking compositions. Such pavement marking compositions are prepared from a two part polyurethane-forming system of a first component having isocyanate-reactive groups (a polyol) and a second component having isocyanate groups. It is disclosed that such compositions dry faster, withstand weathering better, and do not discolor as readily as alkyd-based and epoxy-based compositions. However, the exemplified compositions required aromatic isocyanates in combination with the polyols and a catalyst. Any colorless or lightly colored aromatic polyisocyanate is suggested to increase the reactivity and decrease the viscosity of the isocyanate component and provide a harder polyurethane. Aromatic isocyanates are not particularly desirable because the resultant polyurethanes are subject to environmental degradation and discoloration. Also, many lower molecular weight aromatic isocyanates that would decrease viscosity and modify reactivity or film properties can potentially pose significant inhalation risk or toxic hazard related to their vapor pressure. Furthermore, the use of catalysts is not desirable because they can also catalyze degradation of the polyurethanes. To overcome the deficiencies of aromatic isocyanates, aliphatic isocyanates could be used with polyols; however, this would require the use of a catalyst or an aromatic isocyanate together with an aliphatic isocyanate to obtain sufficient rates of cure.

Thus, the need still exists for liquid pavement marking compositions that can simultaneously provide all of these features in a single material: reduced environmental impact through formulations having low volatile organic content or that are substantially solvent-free; improved balance of coating rheology during application and film formation to promote substrate wet out and fast cure to track-free films; broadened range of weather conditions for coating application; and improved marking performance through increased durability and retained reflectively. Especially needed are liquid pavement marking compositions that resist shrinkage, thus avoiding cracking, coating imperfections and failures.

SUMMARY OF THE INVENTION

We have discovered new secondary amines which react with isocyanates to form stable urea linkages. These amines may be produced cleanly via Michael-type reaction of primary amines with variously substituted male (amide/esters) and fumar (amide/esters).

Accordingly, the present invention in its first aspect includes a novel secondary amine of the formula shown here as formula (IV)

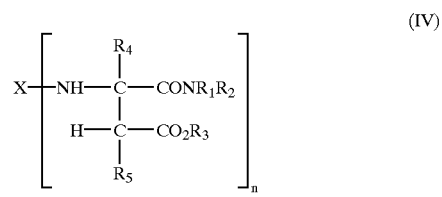

wherein X is alkyl, alkylene, aryl or arylene with a valency of n; $R_1$, $R_2$, $R_4$ and $R_5$ are each independently H, alkyl or aryl; $R_3$ is alkyl or aryl; and n is an integer greater than or equal to 1.

A second aspect of the present invention includes an improved process for preparing amide-ester precursors of the formula (V), shown below, using an organic tin salt as a catalyst.

A third aspect of the present invention is a polyurea coating composition derived from a polyisocyanate component and an isocyanate-reactive component which includes at least one compound corresponding to the novel secondary amines of the present invention.

A fourth aspect of the present invention includes a process of preparing a polyurea coating. This process consists of coating a substrate with a polyisocyanate component and an isocyanate-reactive component which includes at least one compound corresponding to the novel secondary amines of the present invention and then hardening said composition at a temperature ranging from 10° C. to 80° C.

The present invention provides also a two-part liquid pavement marking including a binder having polyurea groups, wherein the binder is prepared from a two-part coating composition containing an amine component including one or more secondary amines as defined above and optionally one or more amine-functional coreactants, and an isocyanate component comprising one or more polyisocyanates. Preferably, the pavement marking includes a binder having urea groups, wherein the binder is prepared from a two-part coating composition containing an amine component including one or more secondary amines as defined above and optionally one or more amine-functional coreactants, and an isocyanate having one or more polyisocyanates, wherein the coating composition has a minimum application temperature of at least about 10° C. and a track free time of no greater than about 5 minutes. Also provided is a traffic bearing surface having thereon such a pavement marking, and a preformed pavement marking wherein the composition is coated on a substrate that can be applied to a traffic bearing surface.

Methods of applying such compositions are also provided. For example, a method of marking a traffic bearing surface is provided. The method includes applying to the traffic bearing surface a two-part coating composition containing an amine component including one or more secondary amines and optionally one or more amine-functional coreactants, and an isocyanate component having one or more polyisocyanates.

DETAILED DESCRIPTION OF THE INVENTION

The secondary amines of the invention are those of formula (IV)

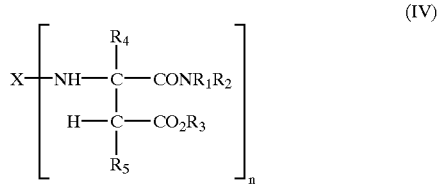

wherein X is alkyl, alkylene, aryl or arylene with a valency of n; $R_1$, $R_2$, $R_4$ and $R_5$ are each independently H, alkyl or aryl; $R_3$ is alkyl or aryl; and n is an integer greater than or equal to 1.

An alkyl group is a paraffinic hydrocarbon group which is derived from an alkane by removing one hydrogen from the formula. The hydrocarbon group may be either linear, branched or cyclic when $R_1$ and $R_2$ are taken together with the nitrogen atom, having 1 to 20 carbon atoms. Preferably, the hydrocarbon has 1 to 5 carbon atoms. Simple examples include methyl (—$CH_3$) and ethyl (—$CH_2CH_3$).

An aryl group is an unsaturated hydrocarbon group having an aromatic ring structure characteristic of benzene, naphthalene, etc. i.e., either the six carbon ring of benzene or the condensed six carbon rings of other aromatic derivatives. The aromatic ring can be either substituted or unsubstituted. Possible substituent groups include alkyl, amino, nitro, hydroxyl, halogen and methoxy groups. A simple example of an aryl group (unsubstituted) is phenyl (—$C_6H_5$).

An isocyanate group is a compound containing the isocyanate radical (—NCO). The term isocyanate refers to a polyisocyanate, preferably a diisocyanate or triisocyanate.

An arylene group is a multivalent radical which is formed by removing hydrogen from at least two carbon sites on an aromatic nucleus.

An alkylene group is an organic radical which is formed by removing hydrogen from at least two carbon sites on an aliphatic hydrocarbon. A simple example is the ethylene radical, —$C_2H_4$—.

As discussed previously, the novel secondary amines of the present invention may be produced via Michael-type reaction of primary amines with various amide-esters. Useful Michael receptors as precursors include adducts of alcohols with isomaleimides. This reaction is illustrated below providing a compound of formula (V).

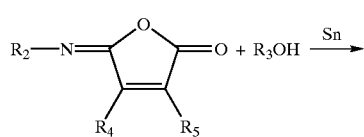

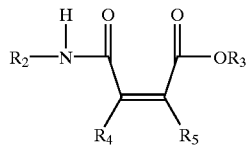

The use of an organotin salt as a catalyst has resulted in increased yields of desired product. The process of the present invention includes reacting the above isomaleimide with an alcohol, $R_3OH$, in the presence of an organotin catalyst to afford a compound of formula V, wherein $R_2$ is an alkyl group or an aryl group and $R_3$, $R_4$, and $R_5$ are as defined above.

The reaction of the isomaleimide with an alcohol can be carried out at from about 0° C. to about 100° C., preferably from ambient temperatures, about 25° C. to about 70° C. Examples of organotin salts employable as catalysts are dibutyltin dilaurate, dibutyltin diacetate, dimethyltin dilaurate, stannous octoate, bis(lauryldibutyltin) oxide, dibutyltin dimercaptide, and dibutyltin dimercaptide. A preferred catalyst is dibutyltin diacetate. The amount of catalyst used may vary from about 0.1 to about 10 mole % based on the amount of alcohol. The isomaleimide starting materials can be prepared by known methods.

An alternate method of preparing amide ester precursors includes reacting a maleic anhydride with an amine followed by converting the carboxylic acid group to the desired ester. This reaction is illustrated below.

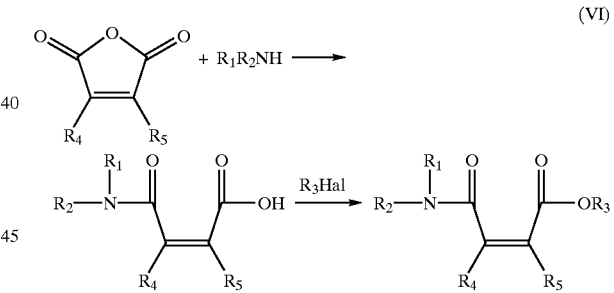

wherein $R_1$, $R_2$, $R_3$, $R_4$ and $R_5$ are as defined above, and Hal represents a halide ion, preferably iodide.

The reaction of a primary amine with an amide-ester Michael receptor is often spontaneous, rapid, and nearly quantitative. The adducts may be synthesized by simply allowing mixtures of primary amines and Michael receptors to stand for about 96 hours at about 70° C. in the absence of catalyst. This reaction is illustrated below.

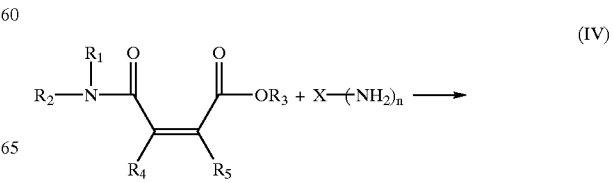

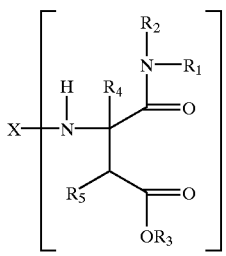

wherein X, n and $R_1$ to $R_5$ are as defined above.

Amines useful in preparing the secondary amines of the present invention include, for example, ethylene diamine, 1,2-diaminopropane, 2,5-diamino-2,5-dimethylhexane, 1,11-diaminoundecane, 1,12-diaminododecane, 2,4'-diamino-dicyclohexyl methane, 1-amino-3,3,5-trimethyl-5-aminomethylcyclohexane, 2,4-or 2,6-diaminotoluene, 2,4'- or 4,4'-diaminodiphenyl methane or mixtures thereof. Amines preferred for preparing the novel secondary amines of the present invention include 1,4-diaminobutane, 1,6-diaminohexane, 2,4,4-trimethyl-1,6-diaminohexane, 1-amino-3,3,5-trimethyl-5-aminomethyl-cyclohexane, 4,4'-diamino-dicyclohexyl methane, 3,3-dimethyl-4,4'-diamino-dicyclohexyl methane or mixtures thereof. Especially preferred amines include 4,4'-methylene-bis(cyclohexylamine), 2-methyl-1,5-pentanediamine, 1,6-diaminohexane and mixtures thereof.

The reaction generally proceeds to 80–99% completion within 96 hours. Since the reactions are clean, purification of the reaction products is not necessary.

These sterically-hindered secondary amines react more controllably with electrophiles than do the corresponding primary amines and hydrogen bonding in their adducts is significantly reduced or eliminated. The novel secondary amines of the present invention react with isocyanates to form urea-amide/ester linkages. This reaction is illustrated below as formula (VII).

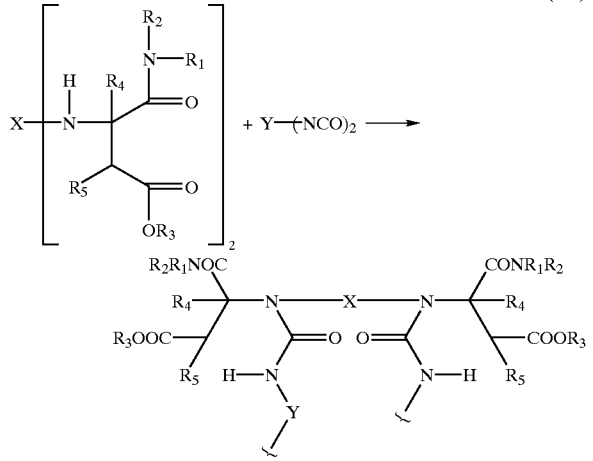

(VII)

wherein X, $R_1$, $R_2$ and $R_3$ are as defined above and Y is X.

Unlike the urea-diester linkages, urea-amide/ester linkages are stable. The amide-ester resists cyclizing to a hydantoin. Hydantoins cause shrinkage and are formed as previously described with urea-diester linkages.

POLYUREA COATINGS

The present invention is further directed to a polyurea coating composition which has a polyisocyanate component and an isocyanate-reactive component which contains at least one compound corresponding to the novel secondary amines of the present invention as defined above. The cross-linking which takes place in the process according to the present invention is based on an addition reaction between the polyisocyanate component and the isocyanate-reactive component, in particular the novel secondary amines of the present invention.

Polyisocyanates include compounds bearing at least one isocyanate group and include known polyisocyanates of polyurethane chemistry. Suitable low molecular weight polyisocyanates having a molecular weight between 168 and 5000 include hexamethylene diisocyanate, 2,2,4-and/or 2,4,4-trimethyl-1,6-hexamethylene diisocyanate, dodecamethylene diisocyanate, 1,4-diisocyanatocyclohexane, 1-isocyanato-3,3,5-trimethyl-5-isocyanatomethylcyclohexane (IPDI), 2,4'-and/or 4,4'-diisocyanato-dicyclohexyl methane, 2,4'-and 4,4'-diisocyanato-diphenyl methane and mixtures of these isomers with their higher homologues which are obtained by the phosgenation of aniline/formaldehyde condensates, 2,4- and/or 2,6-diisocyanatotoluene and any mixtures of these compounds.

It is preferred, however, to use derivatives of these monomeric polyisocyanates. These derivatives include polyisocyanates containing biuret (carbamylurea) groups as described, for example, in U.S. Pat. Nos. 3,124,605, 3,201,372 DE-OS 1,101,394; polyisocyanates containing isocyanurate groups as described, for example, in U.S. Pat. No. 3,001,973, DE-PS 1,022,789, 1,333,067 and 1,027,394 and DE-OS 1,929,034 and 2,004,048; polyisocyanates containing urethane groups as described, for example, in DE-OS 953,012, BE-PS 752,261 and U.S. Pat. Nos. 3,394,164 and 3,644,457; polyisocyanate containing carbodiimide groups as described in DE-OP 1,092,007, U.S. Pat. No. 3,152,162 and DE-OS 2,504,400, 2,537,685 and 2,552,350; and polyisocyanates containing allophanate groups as described, for example, in GB-PS 994,890, BE-PS 761,626 and NL-OS 7,102,524.

The modified polyisocyanates are particularly preferred: N,N', N"-tris-(6-isocyanatohexyl)-biuret and mixtures thereof with its higher homologues and N,N',N"-tris-(6-isocyanatohexyl)-isocyanurate and mixtures thereof with its higher homologues containing more than one isocyanurate ring.

Isocyanate group-containing prepolymers and semi-prepolymers based on the monomeric simple or modified polyisocyanates exemplified above and organic polyhydroxyl compounds are also preferred for use as the polyisocyanate component. These prepolymers and semi-prepolymers generally have about 140–8400 equivalent weight, preferably about 210–420 equivalent weight, and are prepared in known manner by the reaction of the above mentioned starting materials at an NCO/OH equivalent ratio of about 1.05:1 to 10:1 preferably about 1.1:1 to 3:1, this reaction being optionally followed by distillative removal of any unreacted volatile starting polyisocyanates still present.

The prepolymers and semi-prepolymers may be prepared from low molecular weight polyhydroxyl compounds having a molecular weight of 62 to 299, such as ethylene glycol, propylene glycol, trimethylol propane, 1,6-dihydroxy hexane; low molecular weight, hydroxyl-containing esters of these polyols with dicarboxylic acids of the type exemplified hereinafter; low molecular weight ethoxylation and/or propoxylation products of these polyols; and mixtures of the preceding polyvalent modified or unmodified alcohols.

The prepolymers and semi-prepolymers are, however, preferably prepared from the known relatively high molecular weight polyhydroxyl compounds of polyurethane chemistry which have a molecular weight of 300 to about 8000, preferably about 1000 to 5000, as determined by the functionality and the OH number. These polyhydroxyl compounds have at least two hydroxyl groups per molecule and generally have a hydroxyl group content of about 0.5 to 17% by weight.

Examples of suitable relatively high molecular weight polyhydroxyl compounds which may be used for the preparation of the prepolymers and semi-prepolymers include the polyester polyols based on the previously described low molecular weight, monomeric alcohols and polybasic carboxylic acids such as adipic acid, sebacic acid, phthalic acid, isophthalic acid, tetra-hydrophthalic acid, hexahydrophthalic acid, maleic acid, the anhydrides of these acids and mixtures of these acids and/or acid anhydrides. Hydroxyl group-containing polylactones, especially poly-e-caprolactones, are also suitable for the preparation of the prepolymers and semi-prepolymers.

Polyether polyols, which are obtained in known manner by the alkoxylation of suitable starting molecules, are also suitable for the preparation of the isocyanate group-containing prepolymers and semi-prepolymers. Examples of suitable starting molecules for the polyether polyols include the previously described monomeric polyols, water, organic polyamines having at least two NH bonds and any mixtures of these starting molecules. Ethylene oxide and/or propylene oxide are particularly suitable alkylene oxides for the alkoxylation reaction. These alkylene oxides may be introduced into the alkoxylation reaction in any sequence or as a mixture.

Also suitable for the preparation of the prepolymers and semi-prepolymers are the hydroxyl group-containing polycarbonates which may be prepared by the reaction of the previously described monomeric diols with phosgene and diaryl carbonates such as diphenyl carbonate.

These other optionally used isocyanate-reactive compounds are preferably organic polyhydroxyl compounds known from polyurethane chemistry and include both the low molecular weight polyhydroxyl compounds and the relatively high molecular weight polyhydroxyl compounds previously set forth for the preparation of the prepolymers and semi-prepolymers suitable for use as the polyisocyanate component.

Isocyanate-reactive compounds which may be used as a portion of the polyisocyanate component are the hydroxy functional polyacrylates known for use in polyurethane coatings. These compounds are hydroxyl-containing copolymers of olefinically unsaturated compounds having a number average molecular weight ($M_n$) determined by vapor pressure or membrane osmometry of about 800 to 50,000, preferably about 1000 to 20,000 and more preferably about 5000 to 10,000, and having a hydroxyl group content of about 0.11 to 12% by weight, preferably about 1 to 10% by weight and most preferably about 2 to 6% by weight. The copolymers are based on olefinic monomers containing hydroxyl groups and olefinic monomers which are free from hydroxyl groups. Examples of suitable monomers include vinyl and vinylidene monomers such as styrene, a-methyl styrene, o- and p-chloro styrene, o-, m- and p-methyl stryene, p-tert-butyl styrene; acrylic acid; (methy) acrylonitrile; acrylic and methacrylic acid esters of alcohols containing 1 to 8 carbon atoms such as ethyl acrylate, methyl acrylate, n- and isopropyl acrylate, n-butyl acrylate, 2-ethylhexyl acrylate, 2-ethylhexyl methacrylate, iso-octyl acrylate, methyl methacrylate, ethyl methacrylate, butyl methacrylate and iso-octyl methacrylate; diesters of fumaric acid, itatonic acid or maleic acid having 4 to 8 carbon atoms in the alcohol component; (methy)acrylic acid amide; vinyl esters of alkane monocarboxylic acids having 2 to 5 carbon atoms such as vinyl acetate or vinyl propionate; and hydroxyalkyl esters of acrylic acid or methacrylic acid having 2 to 4 carbon atoms in the hydroxyalkyl group such as 2-hydroxyethyl-, 2, hydroxypropyl-, 4-hydroxybutyl-acrylate and methacrylate and trimethylol propane-mono- or pentaerythritomono-acrylate or methyacrylate. Mixtures of the monomers exemplified above may also be used for the preparation of the hydroxy functional polyacrylates. Mixtures of the polyhydroxyl compounds previously described may be used as a portion of the polyisocyanate component.

In the coating compositions to be used for the process according to the invention, the ratio by weight of the total quantity of binder components to the quantity of solvent is about 40:60 to 100:0, preferably about 60:40 to 100:0.

The coating compositions to be used for the process according to the invention may also contain other auxiliary agents and additives conventionally used in polyurethane coatings, in particular pigments, fillers, leveling agents, catalysts, antisettling agents, antioxidants, UV stabilizers and the like.

The properties of the coatings obtained by the process according to the invention may be adjusted, in particular by suitable choice of the nature and proportions of the starting components. Thus, for example, the presence of relatively high molecular weight, linear polyhydroxyl compounds either in the prepolymers or semi-prepolymeyers of each component increases the elasticity of the coatings; whereas, the absence of such starting components increases the crosslinking density and hardness of the resulting coatings.

For carrying out the process according to the invention, the coating compositions to be used according to the invention are applied as one or more layers to substrates by known methods such as spraying, brush coating, immersion or flooding or by means of rollers or doctor applicators. The process according to the invention is suitable for the formation of coatings on any substrates, e.g., metals, plastics, wood or glass. The substrates to be coated by the process according to the invention may be treated with suitable primers before the process according to the invention is carried out.

After the substrates exemplified above have been coated, the coatings are cured by the process according to the invention at a temperature of about −20° to 100° C. Curing is preferably carried out at a temperature of about 10° C. to 80° C.

LIQUID PAVEMENT MARKER

The present invention provides a two-part liquid pavement marking containing a binder having polyurea groups, wherein the binder is prepared from a two-part coating composition having an amine component including one or more novel secondary amines of the present invention as defined above and optionally one or more amine-functional coreactants, and an isocyanate component having one or more polyisocyanates. Preferably, the pavement marking contains a binder having urea groups, wherein the binder is prepared from a two-part coating composition having an amine component with one or more secondary amines and optionally one or more amine-functional coreactants, and an isocyanate component containing one or more polyisocyanates, wherein the coating composition has a minimum application temperature of at least about 10° C. and a track free time of no greater than about 5 minutes.

In the binders used according to the invention, there is an equivalent ratio of isocyanate groups to isocyanate-reactive groups of about 0.8:1 to 20:1, preferably about 0.8:1 to 2:1, more preferably about 0.8:1 to 1.2:1 and most preferably about 1:1. The optional polyhydroxyl compound is present in the amine component in an amount such that up to 20 hydroxyl groups are present for each secondary amino, preferably the equivalent ratio of hydroxyl groups to secondary amino groups is about 10:1 to 1:10.

The binders to be used according to the invention are prepared by mixing the individual components together. Preparation of the binders is carried out solvent-free or in the presence of the solvents conventionally used in polyurethane coatings. It is an advantage of the process according to the invention that the quantity of solvent used may be greatly reduced when compared with that required in known two-component systems.

Examples of suitable solvents include xylene, butyl acetate, methyl isobutyl ketone, methoxypropyl acetate, N-methyl pyrrolidone, petroleum hydrocarbons, isobutanol, butyl glycol, butyoxyethanol, chlorobenzenes and mixtures of such solvents. The alcoholic solvents previously mentioned may be used, provided that the optional polyhydroxyl compounds are not used.

The pavement marking compositions of the present invention contain a binder having urea groups. This binder is prepared from a two-part system that includes an amine compound and an isocyanate component. Preferably, the amine component includes secondary amines. More preferably, the amine component includes the secondary amine of the present invention. Most preferably, the amine component includes one or more amide-ester amines, optionally blended with one or more amine-functional coreactants other than an amide-ester amine. Preferably, the amine-functional coreactants are polymeric polyamines, and more preferably, substantially polymeric diamines. These amine-functional coreactants are selected to balance the properties of the coating during the curing process and in its final form.

The amine and isocyanate components are chosen such that the resultant pavement marking is generally resistant and durable to environmental and vehicular stresses and has good daytime visibility. Preferably, it also has good nighttime visibility. Durability can be evidenced by good adhesion (i.e., anchoring) to a wide variety of substrate surfaces, including concrete, asphalt, and other markings, whether they be markings of the same or different material. It can also be evidenced by good adhesion (i.e., anchoring) of reflective elements to the marking, if they are used. As used herein, "durability" can be determined by applying the pavement marking to a road surface that will be exposed to traffic conditions and monitoring the performance of the marking over time. Reflectivity and whiteness can be measured instrumentally in the field and the resistance of the marking to wear and erosion can be subjectively evaluated. Durable markings have continued presence on the substrate, good visibility, and, preferably, good reflectivity over an extended length of time.

The pavement markings formed from the composition of the present invention preferably are durable (i.e., have a useful life) for at least about two years, more preferably, for at least about three years, and most preferably, for at least about four years. If reflective elements are used, the pavement markings have a retained reflectivity of at least about 100 mcd/m$^2$/lux, and more preferably, at least about 150 mcd/m$^2$/lux, throughout its useful life. As used herein, "retained reflectivity" is used to describe the effectiveness of maintained retroreflective performance of a pavement marker over its useful life. Retroreflectivity is currently typically measured by an instrument in the laboratory at fixed entrance and observation angles, according to ASTM D 4061-94. Recent work (Transportation Research Record 1409 published 1994 by the Transportation Research Board) has shown that the entrance angle at which light is incident and observation angles from which a driver actually views a pavement marking, referred to herein as "approximate driver geometries," are appropriate for measured retroreflective performance of pavement markings.

The amine and isocyanate components are preferably chosen such that the pavement marking composition:

(1) is a liquid with a high solids content (preferably, at least about 75 wt-%, and more preferably, at least about 90 wt-%, based on the total weight of the composition), which is substantially solvent free (preferably, less than about 5 wt-% solvent, based on the total weight of the composition);

(2) has a rapid cure profile, with a track-free time (i.e., a dry time at ambient roadway conditions when the coating is applied) of preferably, no greater than about five minutes, more preferably no greater than about four minutes, and most preferably, no greater than about three minutes, and a useful open time (i.e., the length of time the composition will remain free flowing after application to a surface for adequate substrate wet out and particle or reflective element wicking/anchorage) preferably, an open time of at least about 30 seconds, and more preferably, at least about one minute;

(3) has a broad application window (i.e., it is able to be applied over a wide range of temperatures, with emphasis on use at lower temperatures) preferably, having a minimum application temperature of at least about 45° F., more preferably, at least 40° F., even more preferably, at least about 35° F., and most preferably, at least about 25° F.;

(4) is compatible with two-part static mix or airless high pressure impingement-mix application equipment;

(5) includes commercially available, low-cost raw materials; and (6) is generally storage stable preferably, having a useful shelf-life of at least six months, more preferably, at least one year, and most preferably, at least two years.

Although the pavement marking compositions of the present invention are referred to as two-part systems, a number of additives may also be included. These additives include weathering additives, antioxidants, dispersion and grinding aids, wetting agents, impact modifiers, defoamers, pigments, fillers, extenders, diluents, plasticizers, leveling agents and surfactants.

Pigments are well known in the pavement marking art to impart desired visual appearance properties during the daytime and contribute to the reflective properties of the marking at night. Fillers and extenders can be used to modify flow properties of the liquid coating and can contribute to the bulk volume of the final coating. Fillers may also be used to achieve a particular volume ratio without significantly affecting the reactive chemistry. The pigments, fillers and extenders can have a significant impact on uncured formulation and cured film density, film cure profile and track free time, cured film modulus, coating adhesion to a substrate, response to thermal cycling, abrasion and coating durability.

TRAFFIC-BEARING SURFACES

A method of marking a traffic bearing surface is provided, which includes applying to the traffic bearing surface a two-part coating composition containing an amine component having one or more of the novel secondary amines of the present invention as defined above and optionally one or more amine-functional coreactants, and an isocyanate component containing one or more polyisocyanates.

The two-part coating composition is typically applied using spray coating techniques. Typically, the two components are applied using a spray apparatus which allows mixing immediately prior to exiting from the apparatus. For example, two-component, high pressure, airless, impingement mixing systems can be used.

An example of an airless, impingement mixing spray system is manufactured by Gusmer. The system includes the following components: a proportioning section which meters the components and raises the pressure above about 1500 psi; a heating section to control the viscosity of each component; and an impingement spray gun which combines the two components and allows mixing just prior to atomization.

Another useful system is similar to the impingement unit, except that it uses a static mix tube to achieve blending of the two components. This mix tube contains a number of flights designed to mix the components prior to atomization.

It should be noted that the liquid pavement marking compositions provide polyurea coatings having conventional daytime visibility. They can also function as binders to anchor reflective optical elements. When the reflective elements are glass or ceramic microspheres, they are typically in the range of about 200 μm to about 600 μm and may be incorporated into the coating, or preferably, may be dropped onto the wet coating.

Post-spray applied elements in the form of glass or ceramic microspheres can also be used as a binder filler in addition to providing night time reflectivity. They may function similarly to mineral particulates on the wear surface. Preferably, typical coverage rates are greater than about 4 pounds of glass beads per gallon of paint, more preferably greater than 10 pounds per gallon, even more preferably greater than 25 pounds per gallon and most preferably, greater than 30 pounds per gallon.

WORKING EXAMPLES

Preparation of tert-butylisomaleimide (Z)-4-(tert-butylamino)-4-oxo-2-butenoic Acid

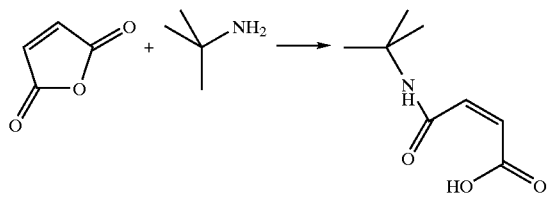

To a 12 L four necked round bottom flask with a mechanical stirrer, thermometer and an addition funnel, under nitrogen, was added 1072.6 grams of maleic anhydride (10.9 moles) and 6062 grams of acetonitrile. The mixture was stirred to dissolve the solids and cooled to −7° C. To this was added 800 grams of t-butylamine (10.9 moles) slowly at a rate such that the temperature remained below 0° C. (approximately 2.5 hour addition). Following the addition the mixture was stirred at −7° C. for one hour and overnight at room temperature. The solid was collected by filtration, washed with 500 mL of acetonitrile and dried to give 1355 grains of (Z)-4-(tert-butylamino)-4-oxo-2-butenoic acid as a white solid. 13-C NMR shows this to be 94.62 wt % (Z)-4-(tert-butylamino)-4-oxo-2-butenoic acid, and 5.38 wt % t-butylamine. This material was used without further purification for the next reaction.

5-(tert-butylamino)-2,5-dihydro-2-furanone

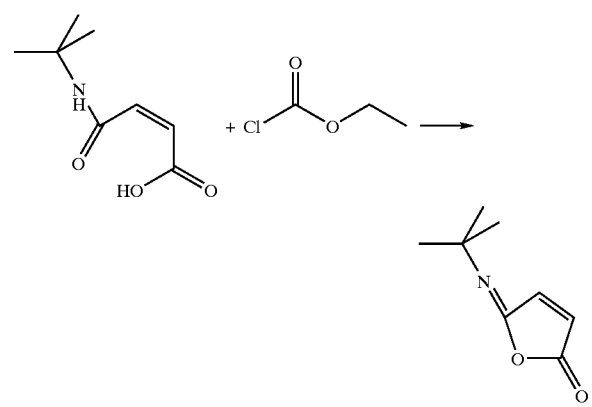

To a 12 liter four necked round bottom flask with a mechanical stirrer, thermometer, addition funnel and condenser, under nitrogen, was added 700 grams of (Z)-4-(tert-butylamino)-4-oxo-2-butenoic acid (4.0 moles) and 7757 grams of dichloromethane. The mixture was cooled to −5° C. and 438.6 grams of ethyl chloroformate (4.0 moles) was added. The mixture was cooled to −10° C. and 408.9 grams of triethylamine (4.0 moles) was added slowly at a rate such that the temperature remained below −7° C. Stirring was continued at −5° C. for 2.5 hours during which time the evolution of carbon dioxide was observed. The mixture was warmed to 11° C. and a premix of 272 grams of sodium bicarbonate dissolved in 3640 grams of distilled water was added. The mixture was stirred for 10 minutes, phase split, and the aqueous phase was removed. The organic phase was extracted three times with 3 L each of distilled water. The organic phase was dried with 275 grams of sodium sulfate, filtered and the solvent was removed in vacuo at 30° C. The residue was purified by distillation (50° C., 0.05 mm Hg) to give 550 grams of 5-(tert-butylimino)-2,5-dihydro-2-furanone. This material is hereinafter referred to as tert-butylisomaleimide. 13-CNMR shows this to be greater than 99% pure.

Preparation of Amide/Ester #1

2.413 grams (40.1 meq.) of anhydrous 2-propanol (Aldrich, Milwaukee, Wis.) was combined with 0.056 grams (0.160 meq.) of dibutyltin diacetate (Air Products, Allentown, Penn.) and mixed for approximately 5 minutes. 6.405 grams (40.1 meq.) of tert-butylisomaleimide was added and mixed for four days at ambient conditions. The product was a low viscosity, clear, yellow colored liquid. ¹H-NMR indicated a yield of 97% of the male(amide-ester) product.

Example 1
Preparation of Secondary Amine 0.777 grams (3.54 meq.) of amide-ester #1 was weighed into a vial. 0.372 grams (3.54 meq.) 4,4'-methylenebis (cyclohexylamine) (PACM-20, Air Products, Allentown, Penn.) was added to the amide-ester and mixed for 10 minutes. The reaction mixture was placed in a 70° C. oven for four days. The product was a viscous, clear, yellow colored liquid. $^1$H-NMR indicated a yield of 90% of the desired amine product.

Example 2
Preparation of Secondary Amine 0.999 grams (4.55 meq.) of amide-ester #1 was weighed into a vial. 0.264 grams (4.54 meq.) 2-methyl-1,5-pentanediamine (Dytek A, DuPont Chemicals, Wilmington, Del.) was added to the amide-ester and mixed for 10 minutes. The reaction mixture was placed in a 70° C. oven for four days. The product was a viscous, clear, yellow colored liquid. $^1$H-NMR indicated a yield of 88% of the desired amine product.

Preparation of Amide/Ester #2

193.50 grams (3.22 eq.) of anhydrous 2-propanol (Aldrich, Milwaukee, Wis.) was combined with 4.34 grams (12.4 meq.) of dibutyltin diacetate (Air Products, Allentown, Penn.) and mixed for approximately 5 minutes. 480.00 grams (3.13 eq.) of tert-butylisomaleimide was added and mixed for one day at ambient conditions followed by three days at 70° C. The product was a low viscosity, clear, yellow colored liquid. $^1$H-NMR indicated a yield of 98.6% of the male(amide-ester) product.

Example 3
Preparation of Secondary Amine 4.927 grams(23.10 meq.) of amide-ester #2 (at 70° C.) was weighed into a vial. 1.342 grams (23.10 meq.) 1,6-diaminohexane at 70° C. (Aldrich, Milwaukee, Wis.) was added to the amide-ester and mixed for 10 minutes. The reaction mixture was placed in a 70° C. oven for 40 hours. The product was a clear, yellow colored liquid. $^1$H-NMR indicated a yield of 95.5% of the desired amine product.

Preparation of Amide/Ester #3

(Z)-4-oxo-4-piperidino-2-butenoic Acid

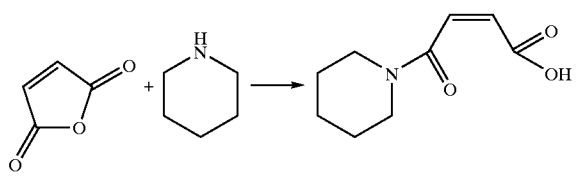

To a 500 mL three necked round bottom flask with a mechanical stirrer, thermometer, and addition funnel, under nitrogen, was added 50 grams (0.51 mmol) of maleic anhydride and 363.7 mL of acetonitrile. The mixture was stirred at room temperature until the solid dissolved and then cooled in an ice bath. To the solution was added 43.4 grams (0.51 mmol) of piperidine at a rate such that the temperature did not go above 20° C. The cooling bath was allowed to melt slowly and the mixture was stirred overnight at room temperature. The solvent was removed in vacuo to give 95.7 grams of a brown solid. 13-C NMR shows this solid to be 88.8 wt % (Z)-4-oxo-4-piperidino-2-butenoic acid, 3.4 wt % acetonitrile, 2.2 wt % maleic anhydride, 4.4 wt % maleic acid and 1.2 wt % of the corresponding fumarate amide or acid. This material was used in the next step without further purification.

Isopropyl (Z)-4-oxo-4-piperidino-2-butenoate

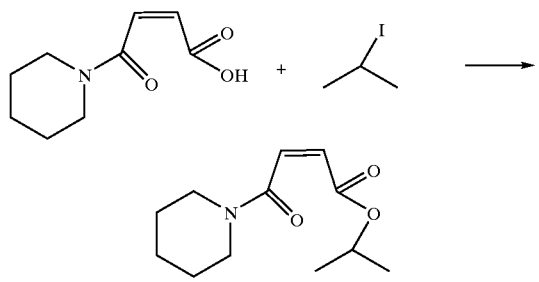

To a 250 mL three necked round bottom flask, under nitrogen, was added 40 grams (0.22 mmol) of (Z)-4-oxo-4-piperidino-2-butenoic acid and 800 mL of acetonitrile. The mixture was stirred at room temperature to dissolve the solid. To this was added 106.71 grams (0.33 mmol) of cesium carbonate and then 111.34 grams (0.66 mmol) of 2-iodopropane was added over a three minute period. The mixture was heated to 80° C. for one hour and cooled to room temperature. To the mixture was added 350 mL of water and 250 mL of ethyl acetate. The mixture was stirred, phase split and the organic phase was separated. The organic phase was extracted two times with 500 mL of water. The organic phase was dried over magnesium sulfate, filtered, and the solvent was removed in vacuo to give 28 grams of a brown liquid. This liquid was distilled on a Kugelrohr (105° C. air temperature, 0.130 mTorr) to give 21.97 grams of a colorless liquid. 13-CNMR shows this to be 94 wt % isopropyl (Z)-4-oxo-4-piperidino-2-butenoate, isopropyl (E)-4-oxo-4-piperidino-2-butenoate, and 2.5 wt % uncharacterized impurities.

Example 4
Preparation of Secondary Amine 0.335 gram (5.766 meq.) of 1,6-diaminohexane (at 70° C., Aldrich, Milwaukee, Wis.) was weighed into a vial. 1.299 grams (5.766 meq.) of amide-ester #3 (at 70° C.) was added to the amine and mixed for 10 minutes. The reaction mixture was placed in a 70° C. oven for 40 hours. The product was a clear, yellow colored liquid. $^1$H-NMR indicated a yield of 90.2% of the desired amine product.

Example 5

Approximately stoichiometric amounts, based on equivalent weights of each material of 4 different diisocyanates and the secondary amine, as described in EXAMPLE 3 were used to prepare coating samples. Because of the rapid cure rate, the secondary amine was first weighed in a beaker. The diisocyanates were then added. The mixture was then vigorously stirred for 15–30 seconds and poured quickly onto a surface to cure. The results are shown in the following table.

TABLE

| Amine Coreactant | Equivalent Weight | Isocyanate | Equivalent Weight | NCO Index | Cure Profile Open Time (Min) | Film Properties |
|---|---|---|---|---|---|---|
| EX 3 | 274 | N-3300 | 194 | 1.05 | <0.5 | High modulus, tough |
| EX 3 | 274 | N-3400 | 194 | 1.05 | <0.5 | High modulus, tough |
| EX 3 | 274 | Desmodur W | 131 | 1.05 | <0.5 | High modulus, brittle |
| EX 3 | 274 | TMXDI | 122 | 1.05 | <0.5 | High modulus, brittle |
| EX3 | 274 | IPDI | 111 | 1.05 | <0.5 | High modulus, v. Brittle |

Raw Material Information:

| Raw Material | Supplier | Product Description |
|---|---|---|
| N-3300 | Bayer Corp. | Polyfunctional aliphatic isocyanate resin based on hexamethylene diisocyanate |
| N-3400 | Bayer Corp. | Polyfunctional aliphatic isocyanate resin based on hexamethylene diisocyanate |
| Desmodur W | Baycr Corp. | Hydrogenated MDI; H12MDI; dicyclohexylmethane, 4,4'-diisocyanate |
| TMXDI | Cytec Industries Inc. | Meta-tetramethylxylylene diisocyanate |
| IPDI | Aldrich Chemical Co. Inc. | Isophorone Diisocyanate |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A process for preparing a compound of the formula

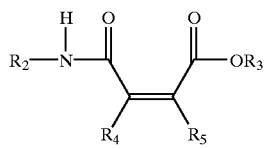

wherein $R_2$ and $R_3$ are alkyl or aryl, and $R_4$ and $R_5$ are each independently hydrogen, alkyl or aryl, which comprises reacting a compound of the formula

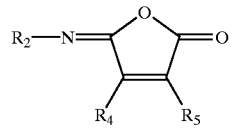

wherein $R_2$, $R_4$ and $R_5$ are as defined above, with a compound of the formula $R_3OH$ in which $R_3$ is as defined above, in the presence of an organotin catalyst.

2. The process of claim 1, wherein the organotin catalyst is selected from dibutyltin dilaurate, dibutyltin diacetate, dimethyltin dilaurate, stannous octoate, bis(lauryl dibutyltin) oxide and dibutyltin dimercaptide.

3. The process of claim 2, wherein the organotin catalyst is dibutyltin diacetate.

4. The process of claim 1, wherein the organotin catalyst is from about 0.1 to about 10 mole % based on the amount of the compound of formula $R_3OH$.

* * * * *